United States Patent [19]
Sugiya et al.

[11] Patent Number: 6,080,885
[45] Date of Patent: Jun. 27, 2000

[54] PROCESS FOR PREPARING A PHOSPHONIUM SALT COMPOUND HAVING AN ACRYL GROUP

[75] Inventors: Masashi Sugiya; Tsutomu Watanabe, both of Tokyo, Japan

[73] Assignee: Nippon Chemical Industrial Co., Ltd., Tokyo, Japan

[21] Appl. No.: 09/153,083

[22] Filed: Sep. 15, 1998

[51] Int. Cl.$^7$ ............................... C07C 69/52; C07F 9/02
[52] U.S. Cl. ................................................. 560/222; 568/9
[58] Field of Search ................................. 560/222; 568/9

[56] References Cited

PUBLICATIONS

Database CAPLUS on STN, Acc. No. 1997:650195, Sugiya et al., 'Manufacture of (meth)acryl group–containing phosphonium salts.' JP 09255694 abstract, 1997.
Database CAPLUS on STN, Acc. No. 1995:490030, Hashimoto et al., 'Preparation of antimicrobial phosphonium bromide compounds containing acryl groups.' JP 07025714 (abstract), 1995.

*Primary Examiner*—Gary Geist
*Assistant Examiner*—Brian J. Davis
*Attorney, Agent, or Firm*—Oblon, Spivak, McClelland, Maier & Neustadt, P.C.

[57] ABSTRACT

A phosphonium salt compound having an acryl group which is represented by the following general formula (3) can be made in simple operations:

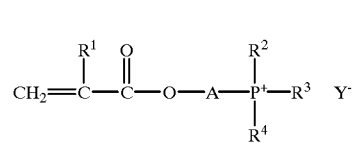

(3)

(wherein A represents a alkylene group, Y represents Cl, Br or I, $R^1$ represents H or $CH_3$, and $R^2$, $R^3$ and $R^4$ represent a alkyl group having 1–8 carbon atoms, cycloalkyl, aryl, alkaryl or aralkyl group) by reacting an unsaturated aliphatic carboxylic acid halide of the following general formula (1):

$$CH_2\!=\!CR^1\!-\!COX \qquad (1)$$

(wherein $R^1$ represents H or $CH_3$ and X represents Cl, Br or I) with a hydroxyalkyl phosphonium salt compound of the following general formula (2):

$$[HO\!-\!A\!-\!P^+R^2R^3R^4]Y^- \qquad (2)$$

(wherein A, Y, $R^2$, $R^3$ and $R^4$ have the same meanings as defined above). The present invention is industrially advantageous since the product can have a very high purity and be obtained in high yield by an easy operation.

3 Claims, No Drawings

PROCESS FOR PREPARING A PHOSPHONIUM SALT COMPOUND HAVING AN ACRYL GROUP

BACKGROUND OF THE INVENTION

1. Field of the Invention

The present invention relates to a phosphonium salt compound having an acryl group, which is a raw material for producing a cationic polymer and is useful as an antistatic agent, an antibacterial agent and the like.

2. Discussion of the Background

A phosphonium salt compound having an acryl group is useful as a raw material for producing a cationic polymer. Unlike a quaternary ammonium salt which is also a cationic compound, the monomer and polymer of the phosphonium salt compound having an acryl group has excellent heat resistance and chemical stability due to firm P—C bond, and recently their potential uses and applications in many fields have been actively examined. For example, a polymeric immobilized antibacterial agent (Japanese Patent Laid-Open No. 7-25714), antibacterial inorganic powder (Japanese Patent Laid-Open No. 7-145014), and antibacterial sol (Japanese Patent Laid-Open No. 7-187928) and the like have been disclosed. An antistatic agent that takes advantage of its cationic property have also been proposed.

Such compounds are usually synthesized according to the following reaction formula (A) or (B).

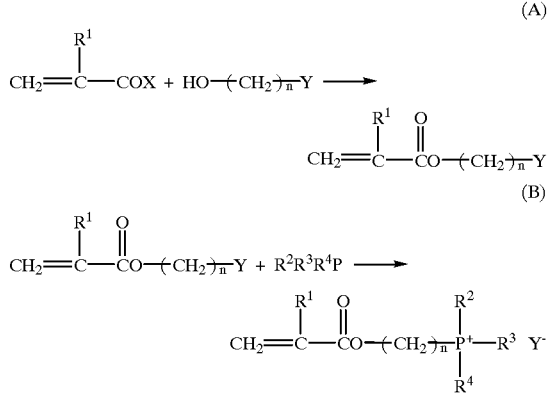

Nevertheless, when a basic catalyst such as pyridine and triethylamine is used for the above-mentioned first reaction (A), the product must be purified and separated from the catalyst by distillation. Therefore, the yield becomes inferior and the procedure is also very complicated. Moreover, when the alkylene chain is lengthened, the boiling point of the product is increased, which restricts the compounds from being synthesized.

Further, in the second reaction (B) wherein the above-mentioned halide having the acryl group is allowed to react with the triorganophosphine, elevated reaction temperatures and long reaction times are required. In addition, when a compound having a polymerizable functional group is synthesized a polymerization inhibitor is normally added, but a polymerized substance and an unreacted substance tend to be mixed in the obtained product when heating at an elevated temperature for a long period of time, and a product with high purity can not be obtained.

In consideration of the above-mentioned situation, as a result of an extensive study to produce a phosphonium salt having an acryl group with high purity, in a high yields and with a simple procedure, the present inventors have found that the phosphonium salt compound having an acryl group with high purity can be easily obtained by reacting a hydroxyalkyl trialkyl phosphonium halide with an unsaturated aliphatic carboxylic acid halide, and achieved the present invention.

Accordingly, an object of the present invention is to provide an industrially advantageous process for preparing a phosphonium salt having an acryl group which allows for the production of a homopolymer or a copolymer.

SUMMARY OF THE INVENTION

Accordingly, the present invention provides a process for preparing a phosphonium salt compound having an acryl group, wherein an unsaturated aliphatic carboxylic acid halide of the following general formula (1):

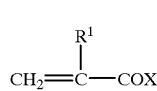

(1)

(wherein $R^1$ represents H or $CH_3$ and X represents Cl, Br or I) is allowed to react with a hydroxyalkyl phosphonium salt compound of the following general formula (2):

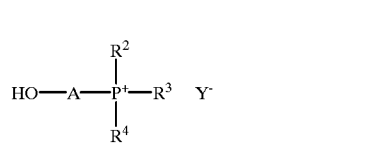

(2)

(wherein A represents a linear or branched alkylene group, Y represents Cl, Br or I, and $R^2$, $R^3$ and $R^4$ represent a linear or branched alkyl group having 1–8 carbon atoms, cycloalkyl group, aryl group, alkaryl group or aralkyl group, optionally substituted by a hydroxy group or alkoxy group, these substituents can be the same or different groups) to produce a phosphonium salt compound having an acryl group which is represented by the following general formula (3):

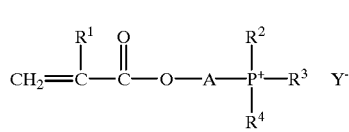

(3)

(wherein A, $R^1$, $R^2$, $R^3$, $R^4$ and Y have the same meanings as defined above).

According to the preparation process of the present invention, the reaction raw materials of the above-mentioned general formula (1) and the above-mentioned general formula (2), i.e. an unsaturated carboxylic acid halide and an alcoholic hydroxyl group are subjected to an esterification reaction, a reaction catalyst is not required and the reaction proceeds at a relatively low temperature in a short time. It is industrially advantageous since the product can have a very high purity and be obtained in high yield by an easy operation.

DETAILED DESCRIPTION OF THE INVENTION

The present invention will hereinafter be explained in more detail.

3

(Unsaturated Fatty Acid Halides)

Unsaturated fatty acid halides of the general formula (1) used as a raw material according to the present invention are not especially limited as long as they are industrially available. Among them, acrylic acid chloride and methacrylic acid chloride are particularly preferable.

(Hydroxyalkyl Phosphonium Salts)

In reference to another raw material, the hydroxyalkyl phosphonium salt compounds of general formula (2), A in the formula represents a linear or branched alkylene such as methylene, ethylene, trimethylene, tetramethylene, pentamethylene, and ethylethylene, and preferably is a linear alkylene having 1–4 carbon atoms. $R^2$, $R^3$ and $R^4$ represent an alkyl such as methyl, ethyl, propyl, butyl, pentyl, hexyl, heptyl, octyl, dodecyl, and octadecyl; an aryl or alkaryl such as phenyl, tolyl, and xylyl; an aralkyl such as benzyl and phenytyl; and the groups obtained by substituting the above-mentioned alkyl, aryl and aralkyl with hydroxy or alkoxy, and among them, an alkyl such as ethyl, butyl and octyl, an aryl such as phenyl and tolyl are particularly preferable, but an alkyl is more preferable. $R^1$, $R^2$ and $R^3$ can be the same or different groups.

$Y^-$ represents a halogen ion such as $Cl^-$, $Br^-$ and $I^-$. $Cl^-$ and $Br^-$ are particularly preferable.

The raw materials for the reaction of the above-mentioned general formula (2) are not particularly limited as long as they are industrially available, and the following are two typical known processes for preparing them.

(1) When A is methylene, a triorganophosphine represented by the following general formula (4):

$$R^2R^3R^4P \quad (4)$$

(wherein $R^2$, $R^3$ and $R^4$ have the same meanings as given above) is allowed to react with paraformaldehyde in the presence of hydrogen halide to give a hydroxyalkyl phosphonium, which is the raw material compound (2), according to the following reaction formula (C):

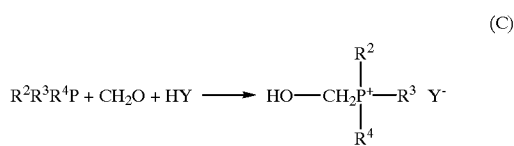

(C)

[Hellmann, H. J. Bader, H. Birkner, and O. Schumacher, Ann., 659, 49 (1962)].

(2) When A is ethylene, trimethylene or tetramethylene and the like, a triorganophosphine of the above-mentioned general formula (4) is allowed to react with a halogenated alkyl alcohol of the following general formula (5):

$$HO—A—Y \quad (5)$$

(wherein A and Y have the same meanings as given before) to give a hydroxyalkyl phosphonium salt, which is the raw material compound (2), according to the following reaction formula (D):

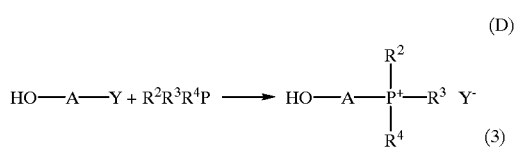

(D)

(3)

[Petrov, K., A. Gavriliva, V. Nam, and V. Chuchkanova, Zh. Obsheh. Khim., 32, 3711 (1962)].

4

(Reaction Conditions)

The present invention can be easily achieved by reacting a compound of the general formula (1) and a compound of the general formula (2). According to the present invention, such raw materials are used to carry out an esterification reaction between an unsaturated carboxylic acid halide and a phosphonium salt having an alcoholic hydroxyl group as shown by the following reaction formula (E), no reaction catalyst is required and the reaction is completed at a relatively low temperature in a short time. This process is extremely advantageous industrially since a product of very high purity can be obtained in high yield by an easy operation.

In the following reaction formula (E) which represents the reaction of the present invention, the reaction temperature is not restricted and usually is 0–100° C., preferably 30–80° C., and the reaction time is normally 1–24 hours, preferably 1–10 hours. If necessary, a maturation reaction can be carried out.

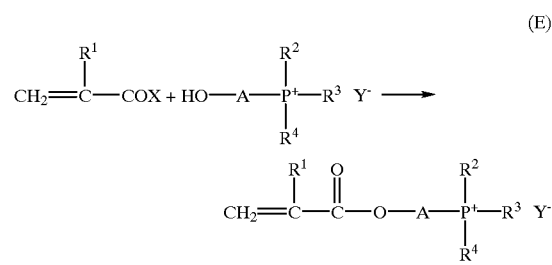

(E)

An appropriate molar ratio of the unsaturated aliphatic carboxylic acid halide of the general formula (1) to the hydroxyalkyl phosphonium salt compound of the general formula (2) for the reaction is 1:1–1:5, preferably 1:1–1:3.

If necessary, a polymerization inhibitor and a reaction solvent are added to carry out the reaction. Examples of the polymerization inhibitors include hydroquinone, hydroquinone monomethyl ether, phenothiazine, 2,6-di-tert-butyl-p-cresol, thiourea, urea, N-phenyl-N'-isopropyl-p-phenylenediamine and the like, but the polymerization inhibitors are not particularly limited to these compounds.

The amount of the polymerization inhibitor added is usually 100–10,000 ppm, preferably 50–5,000 ppm based on the desired product, and the amount of the solvent is normally 2–10 times, preferably around 2–5 times, by weight that of the phosphonium salt, but these are not particularly limited.

Examples of the solvent include nitrile compounds such as acetonitrile, propionitrile, and butyronitrile, aromatic hydrocarbons such as toluene, benzene and xylene, aliphatic hydrocarbons such as hexane, heptane, and cyclohexane, ketones such as acetone, methylethylketone, and MIBK, and DMSO, sulfolane, THF, DMF, and dimethylacetamide and the like, but is not particularly limited.

The amount of the above-mentioned solvent is not particularly limited as long as the phosphonium salt, which is the raw material, can be dissolved. However, azeotropic dehydration is desirable to remove trace amounts of water from the solvent and the raw materials. The water content in the reaction system after the azeotropic dehydration is 10–1000 ppm, preferably 10–100 ppm.

(Phosphonium Salt Compound Having an Acryl Group)

Examples of the phosphonium salt compound having an acryl group represented by the general formula (3) obtained by the above-mentioned preparation process include, tri-n-butyl(methacryloyloxymethyl)-phosphonium chloride, trin-butyl(acryloyloxymethyl)phosphonium chloride, tri-n-butyl(2-methacryloyloxyethyl)phosphonium chloride, tri-n-butyl(2-acryloyloxyethyl)phosphonium chloride, tri-n-octyl (2-methacryloyloxyethyl)phosphonium chloride, triethyl(2-methacryloyloxyethyl)phosphonium chloride, tri-n-butyl(2-methacryloyloxyethyl)phosphonium bromide, tri-n-butyl(2-acryloyloxyethyl)phosphonium bromide, tri-n-butyl(2-methacryloyloxyethyl)phosphonium iodide, tri-n-butyl(3-methacryloyloxypropyl)phosphonium chloride, tri-n-butyl(3-acryloyloxypropyl)phosphonium chloride, tri-n-butyl(4-methacryloyloxybutyl)phosphonium chloride, tri-n-butyl(4-acryloyloxybutyl)phosphonium chloride, tricyclohexyl(2-methacryloyloxyethyl)phosphonium chloride, triphenyl(2-methacryloyloxyethyl)phosphonium chloride, tribenzyl(2-methacryloyloxyethyl)phosphonium chloride, tri-p-toluyl (2-methacryloyloxyethyl)phosphonium chloride and the like.

The compound of the present invention is useful in various industrial fields and can be used, for example, for preventing and controlling slime in a paper making process, or for imparting antiseptic property, antibacterial properties, antistatic properties, flame resistant properties and antifouling properties to water, oil/fat, emulsions, paper, wood, rubber, plastics, fiber, film, paint and the like.

The present invention are illustrated with reference to the following examples, but the invention is not intended to be limited only thereto.

EXAMPLE 1

Preparation of tri-n-butyl(methacryloyloxymethyl) phosphonium chloride

A 1 L-four-necked flask equipped with a stirrer, a thermometer, a dropping funnel, and a condenser was sufficiently purged with nitrogen, and 150 g (0.741 mol) of tri-n-butylphosphine, 23.4 g (0.779 mol) of paraformaldehyde, and 200 ml of pure water were added. At a room temperature, 162 g (0.779 mol) of (1+1) hydrochloric acid aqueous solution was gradually added dropwise over 30 minutes, the internal temperature rose to 38° C., and then the solution was maturated at 60° C. for 2 hours. The presence of residual trialkylphosphine in the reaction solution was tested using carbon disulfide, but trialkylphosphine was not detected. The solution was concentrated using an evaporator and then dried with a vacuum pump to give 201.8 g of a white solid. The melting point could not be measured as the substance was highly deliquescent. The purity obtained by a nonaqueous titration using perchloric acid was 98.7% and the yield was 100%.

Into a 1 L-four-necked flask equipped with a stirrer, a thermometer and a distillation line, was added the obtained tri-n-butyl(hydroxymethyl)phosphonium chloride dissolved in 500 ml of acetonitrile. The solution was heated under a normal pressure with stirring and about 200 ml of acetonitrile was distilled. The purpose of this procedure was to remove trace amounts of water in the system by the azeotropic dehydration. The distillation line was replaced with a condenser having a calcium chloride tube, 1.5 g of hydroquinone monomethyl ether was added as a polymerization inhibitor, and 77.5 g (0.741 mol) of methacryloyl chloride was added thereto dropwise through a dropping funnel at 50° C. over 2 hours. The reaction temperature barely rose. Then, the solution was maturated for 3 hours at the same temperature.

After cooling, a part of the reaction solution was taken out and analyzed by FT-IR, but no OH stretching vibration of the hydroxyl group or C=O stretching vibration of methacryloyl chloride attributable to the raw material was observed, and C=O stretching vibration attributable to the carboxylic ester was newly recognized. The reaction was thus judged to have been completed. The reaction solution was concentrated and dried with a vacuum pump to give 254.2 g of a slightly yellow viscous liquid. The titration purity was 97.4% and the yield was 99.2%.

The identification of the product was carried out by FAB-MS(Pos.);301, FAB-MS(Neg.);35, 37.

EXAMPLE 2

Preparation of tri-n-butyl(acryloyloxymethyl) phosphonium chloride

The above-mentioned compound was synthesized in a procedure similar to that of Example 1 except that 67.1 g (0.741 mol) of acryloyl chloride was used instead of methacryloyl chloride. 241.2 g of a slightly yellow viscous liquid was obtained. The titration purity was 98.1% and the yield was 98.9%.

The identification of the product was carried out by FAB-MS(Pos.);287, FAB-MS(Neg.);35, 37.

EXAMPLE 3

Preparation of tri-n-butyl(2-methacryloyloxyethyl) phosphonium chloride

A 500 ml-four-necked flask equipped with a stirrer, a thermometer, a dropping funnel, and a condenser was sufficiently purged with nitrogen, and 150 g (0.741 mol) of tri-n-butylphosphine was added. At 80° C., 62.7 g (0.779 mol) of 2-chloroethanol was added dropwise over 30 minutes, and the solution turned white and cloudy with the dropping of the agent. Then, the solution was maturated at 120° C. for 2 hours. The reaction solution was an extremely viscous colorless and transparent liquid. The presence of unreacted trialkylphosphine was tested using carbon disulfide, but trialkylphosphine was not detected. The solution was concentrated using an evaporator and then dried with a vacuum pump to give 206.4 g of a colorless and transparent viscous liquid. The titration purity was 100.0% and the yield was 98.5%.

Into a 1 L-four-necked flask equipped with a stirrer, a thermometer and a distillation line, was added the obtained tri-n-butyl(2-hydroxyethyl)phosphonium chloride dissolved in 500 ml of acetonitrile. The solution was heated under a normal pressure while stirring and about 200 ml of acetonitrile was distilled. A condenser having a calcium chloride tube was installed, 1.5 g of hydroquinone monomethyl ether was added as a polymerization inhibitor, and 76.3 g (0.730 mol) of methacryloyl chloride was added thereto dropwise at 50° C. over 2 hours through a dropping funnel, then the solution was maturated for 3 hours at the same temperature.

The absence of an unreacted substance was confirmed by FT-IR, and the reaction solution was concentrated and dried with a vacuum pump to give 249.3 g of a slightly yellow viscous liquid. The titration purity was 96.9% and the yield was 94.3%.

The identification of the product was carried out by FAB-MS(Pos.);315, FAB-MS(Neg.);35, 37.

EXAMPLE 4

Preparation of tri-n-butyl(2-acryloyloxyethyl) phosphonium chloride 241.6 g of a slightly yellow viscous liquid was obtained in a procedure similar to that of Example 3 except that 66.1 g (0.730 mol) of acryloyl chloride was used instead of methacryloyl chloride. The titration purity was 97.6% and the yield was 95.9%.

The identification of the product was carried out by FAB-MS(Pos.);301, FAB-MS(Neg.);35, 37.

EXAMPLE 5

Preparation of tri-n-octyl(2-methacryloyloxyethyl) phosphonium chloride

A 500 ml-four-necked flask equipped with a stirrer, a thermometer, a dropping funnel, and a condenser was sufficiently purged with nitrogen and 150 g (0.405 mol) of tri-n-octylphosphine and 39.1 g (0.486 mol) of 2-chloroethanol were added. They were not miscible with each other and separated into two phases and no exothermic reaction was observed. The temperature was gradually raised under nitrogen stream while stirring and finally the reaction was carried out at 150° C. for 8 hours. After cooling, the presence of residual trialkylphosphine in the reaction solution was tested using carbon disulfide but the trialkylphosphine was not detected. The reaction solution was concentrated using an evaporator then dried with a vacuum pump to give 190.1 g of a waxy white solid. The titration purity was 96.1% and the yield was 100.0%.

Into a 1 L-four-necked flask equipped with a stirrer, a thermometer and a distillation line, was added the obtained tri-n-octyl(2-hydroxyethyl)phosphonium chloride dissolved in 500 ml of acetonitrile. The solution was heated under a normal pressure while stirring and about 200 ml of acetonitrile was distilled. A condenser having a calcium chloride tube was installed, 1.5 g of hydroquinone monomethyl ether was added as a polymerization inhibitor, and 42.3 g (0.405 mol) of methacryloyl chloride was added thereto dropwise at 50° C. over 2 hours through a dropping funnel, then the solution was maturated for 3 hours at the same temperature as above. The absence of an unreacted substance was confirmed by FT-IR, and the reaction solution was concentrated and dried with a vacuum pump to give 209.2 g of a slightly yellow viscous liquid. The titration purity was 97.1% and the yield was 96.6%.

The identification of the product was carried out by FAB-MS(Pos.);483, FAB-MS(Neg.);35, 37.

EXAMPLE 6

Preparation of triethyl(2-methacryloyloxyethyl) phosphonium chloride

A 1 L-four-necked flask equipped with a stirrer, a thermometer, a dropping funnel, and a condenser was sufficiently purged with nitrogen, and 100 g (0.846 mol) of triethylphosphine and 400 ml of toluene were added. At 80° C., 74.9 g (0.930 mol) of 2-chloroethanol was added thereto dropwise over 1 hour. Then, maturation was carried out at 100° C. for 3 hours. The presence of residual trialkylphosphine in the reaction solution was tested using carbon disulfide, but trialkylphosphine was not detected. The solution was concentrated using an evaporator and then dried with a vacuum pump to give 165.0 g of a colorless and transparent viscous liquid. The titration purity was 99.0% and the yield was 97.2%.

A distillation line was installed instead of the condenser and the obtained tri-n-butyl(2-hydroxyethyl)phosphonium chloride was dissolved in 500 ml of acetonitrile. The solution was heated under a normal pressure while stirring and about 200 ml of acetonitrile was distilled. A condenser having a calcium chloride tube was installed, 1.5 g of hydroquinone monomethyl ether was added as a polymerization inhibitor, and 85.9 g (0.822 mol) of methacryloyl chloride was added thereto dropwise at 50° C. over 2 hours through a dropping funnel, then the solution was maturated for 3 hours at the same temperature.

The absence of an unreacted substance was confirmed by FT-IR, and the reaction solution was concentrated and dried with a vacuum pump to give 214.7 g of a slightly yellow viscous liquid. The titration purity was 98.2% and the yield was 96.1%.

The identification of the product was carried out by FAB-MS(Pos.);231, FAB-MS(Neg.);35, 37.

EXAMPLE 7

Preparation of tri-n-butyl(2-methacryloyloxyethyl) phosphonium bromide

A thermometer, our-necked flask equipped with a stirrer, a thermometer, a dropping funnel, and a condenser was sufficiently purged with nitrogen, and 150 g (0.741 mol) of tri-n-butylphosphine was added. At 50° C., 97.3 g (0.779 mol) of 2-bromoethanol was added dropwise over 30 minutes, and then the solution was maturated at 120° C. for 2 hours. The presence of residual trialkylphosphine in the reaction solution was tested using carbon disulfide, but trialkylphosphine was not detected. The solution was concentrated using an evaporator then dried with a vacuum pump to give 237.4 g of a colorless and transparent viscous liquid. The titration purity was 99.4% and the yield was 97.3%.

Into a 1 L-four-necked flask equipped with a stirrer, a thermometer and a distillation line, was added the obtained tri-n-butyl(2-hydroxyethyl)phosphonium bromide dissolved in 500 ml of acetonitrile. The solution was heated under a normal pressure with stirring and about 200 ml of acetonitrile was distilled out. A condenser having a calcium chloride tube was installed and 1.5 g of hydroquinone monomethyl ether was added as a polymerization inhibitor, and 75.8 g (0.725 mol) of methacryloyl chloride was added thereto dropwise at 50° C. over 2 hours through a dropping funnel, then the solution was maturated for 3 hours at the same temperature.

The absence of an unreacted substance was confirmed by FT-IR, and the reaction solution was concentrated and dried with a vacuum pump to give 297.8 g of a slightly yellow viscous liquid. The titration purity was 94.5% and the yield was 98.7%.

The identification of the product was carried out by FAB-MS(Pos.);315, FAB-MS(Neg.);79, 81.

EXAMPLE 8

Preparation of tri-n-butyl(2-acryloyloxyethyl) phosphonium bromide 278.1 g of a slightly yellow viscous liquid was obtained in a procedure similar to that of Example 7 except that 65.6 g (0.725 mol) of acryloyl chloride was used instead of methacryloyl chloride. The titration purity was 95.6% and the yield was 96.7%.

The identification of the product was carried out by FAB-MS(Pos.);301, FAB-MS(Neg.);79, 81.

EXAMPLE 9

Preparation of tri-n-butyl(2-methacryloyloxyethyl)- phosphonium iodide

A 500 ml-four-necked flask equipped with a stirrer, a thermometer, a dropping funnel, and a condenser was sufficiently purged with nitrogen, and 150 g (0.741 mol) of tri-n-butylphosphine was added. 127.4 g (0.741 mol) of 2-iodoethanol was added thereto dropwise over about 1 hour while the temperature was kept at 50 to 55° C., then the solution was maturated at 80° C. for 2 hours. The presence of residual trialkylphosphine in the reaction solution was tested using carbon disulfide, but trialkylphosphine was not detected. The solution was concentrated using an evaporator then dried with a vacuum pump to give 273.5 g of a waxy white solid having a melting point of 43.6 to 45.2° C. The substance was almost totally undeliquescent. The titration purity was 100.0% and the yield was 98.6%.

Into a 1 L-four-necked flask equipped with a stirrer, a thermometer and a distillation line, was added the obtained tri-n-butyl(2-hydroxyethyl)phosphonium iodide dissolved in 500 ml of acetonitrile. The solution was heated under a normal pressure with stirring and about 200 ml of acetonitrile was distilled. A condenser having a calcium chloride tube was installed, 1.5 g of hydroquinone monomethyl ether was added as a polymerization inhibitor, and 76.4 g (0.731 mol) of methacryloyl chloride was added thereto dropwise at 50° C. over 2 hours through a dropping funnel, then the solution was maturated for 3 hours at the same temperature. Upon dropping, yellow coloration that was believed to have been caused by isolation of iodine occurred.

The absence of an unreacted substance was confirmed by FT-IR, and the reaction solution was concentrated and dried with a vacuum pump to give 309.6 g of a reddish brown viscous liquid. The titration purity was 95.2% and the yield was 95.5%.

The identification of the product was carried out by FAB-MS(Pos.);315, FAB-MS(Neg.);127.

EXAMPLE 10

Preparation of tri-n-butyl(3-methacryloyloxypropyl)-phosphonium chloride

A 500 ml-four-necked flask equipped with a stirrer thermometer, a dropping funnel, and a condenser was sufficiently purged with nitrogen, and 150 g (0.741 mol) of tri-n-butylphosphine was added. At 80° C., 73.6 g (0.779 mol) of 3-chloro-1-propanol was added thereto, the temperature was raised stepwise and the solution was finally heated at 150° C. for 4 hours. The presence of residual trialkylphosphine in the reaction solution was tested using carbon disulfide, and trialkylphosphine was not detected. The solution was concentrated using an evaporator then dried with a vacuum pump to give 220.0 g of a colorless and transparent viscous liquid. The titration purity was 97.8% and the yield was 97.8%.

Into a 1 L-four-necked flask equipped with a stirrer, a thermometer and a distillation line, was added the obtained tri-n-butyl(3-hydroxypropyl)phosphonium chloride dissolved in 500 ml of acetonitrile. The solution was heated under a normal pressure while stirring and about 200 ml of acetonitrile was distilled. A condenser having a calcium chloride tube was installed, 1.5 g of hydroquinone monomethyl ether was added as a polymerization inhibitor, and 75.8 g (0.725 mol) of methacryloyl chloride was added dropwise at 50° C. over 2 hours through a dropping funnel, then the solution was maturated for 3 hours at the same temperature as above. The absence of an unreacted substance was confirmed using FT-IR, and the reaction solution was concentrated and dried with a vacuum pump to give 290.3 g of a slightly yellow liquid. The titration purity was 94.6% and the yield was 100.0%.

The identification of the product was carried out by FAB-MS(Pos.);343, FAB-MS(Neg.);35,37.

EXAMPLE 11

Preparation of tri-n-butyl(3-acryloyloxypropyl) phosphonium chloride 271.9 g of a slightly yellow liquid was obtained in a procedure analogous to that of Example 3 except that 65.6 (0.725 mol) of acryloyl chloride was used instead of methacryloyl chloride. The titration purity was 96.8% and the yield was 99.5%.

The identification of the product was carried out by FAB-MS(Pos.);329, FAB-MS(Neg.);35, 37.

EXAMPLE 12

Preparation of tri-n-butyl(4-methacryloyloxybutyl) phosphonium chloride

A 500 ml-four-necked flask equipped with a stirrer, a thermometer, a dropping funnel, and a condenser was sufficiently purged with nitrogen, and 150 g (0.741 mol) of tri-n-butylphosphine was added. At 140° C., 62.7 g (0.779 mol) of 4-chloro-1-butanol was added thereto gradually dropwise over 4 hours while preventing reflux, and then the solution was maturated at the same temperature as above for 3 hours. A reaction check using carbon disulfide showed that the solution turned red, so unreacted trialkylphosphine was detected. Accordingly, the solution was dissolved in 500 ml of pure water and extracted and washed with 300 ml of toluene to remove unreacted tri-n-butyl phosphine. The aqueous phase was concentrated using an evaporator then dried with a vacuum pump to give 209.9 g of a colorless and transparent viscous liquid. The titration purity was 99.8% and the yield was 90.9%.

Into a 1 L-four-necked flask equipped with a stirrer, a thermometer and a distillation line, was added the obtained tri-n-butyl(4-hydroxybutyl)phosphonium chloride dissolved in 500 ml of acetonitrile. The solution was heated under a normal pressure while stirring and about 200 ml of acetonitrile was distilled. A condenser having a calcium chloride tube was installed, 1.5 g of hydroquinone monomethyl ether was added as a polymerization inhibitor, and 70.5 g (0.674 mol) of methacryloyl chloride was added thereto dropwise at 50° C. over 2 hours through a dropping funnel, then the solution was maturated for 3 hours at the same temperature.

The absence of an unreacted substance was confirmed using FT-IR, and the reaction solution was concentrated and dried with a vacuum pump to give 261.4 g of a slightly yellow viscous liquid. The titration purity was 95.7% and the yield was 98.0%.

The identification of the product was carried out by FAB-MS(Pos.);343, FAB-MS(Neg.);35,37.

EXAMPLE 13

Preparation of tri-n-butyl(4-acryloyloxybutyl) phosphonium chloride 248.1 g of a slightly yellow liquid was obtained in a procedure analogous to that of Example 3 except that 61.0 g (0.674 mol) of acryloyl chloride was used instead of methacryloyl chloride. The titration purity was 96.2% and the yield was 97.1%.

The identification of the product was carried out by FAB-MS(Pos.);357, FAB-MS(Neg.);35, 37.

What is claimed is:

1. A process for preparing a phosphonium salt compound having an acryl group, which comprises reacting an unsaturated aliphatic carboxylic acid halide of the following general formula (1):

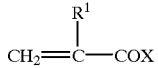
(1)

(wherein $R^1$ represents H or $CH_3$ and X represents Cl, Br or I) with a hydroxyalkyl phosphonium salt compound of the following general formula (2):

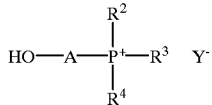
(2)

(wherein A represents a linear or branched alkylene group, Y represents Cl, Br, or I, $R^2$, $R^3$ and $R^4$ represent a linear or branched alkyl group having 1–8 carbon atoms, cycloalkyl group, aryl group, alkaryl group or aralkyl group, optionally substituted by a hydroxy group or alkoxy group, these substituents can be the same or different groups) to produce a phosphonium salt compound having an acryl group which is represented by the following general formula (3):

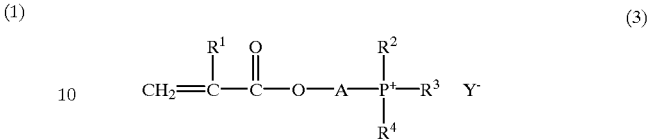
(3)

(wherein A, $R^1$, $R^2$, $R^3$, $R^4$ and Y have the same meanings as defined above).

2. A process according to claim 1, wherein unsaturated aliphatic acid halide is selected from a group consisted of acrylic acid chloride, acrylic acid bromide, methacrylic acid chloride and methacrylic acid bromide.

3. A process according to claim 1 or 2, wherein A in the general formula (2) represents an alkylene group having 1–8 carbon atoms, and $R^2$, $R^3$ and $R^4$ in the general formula (2) represent an alkyl group having 1–8 carbon atoms.

* * * * *